(12) United States Patent
Clippert

(10) Patent No.: US 11,986,377 B2
(45) Date of Patent: *May 21, 2024

(54) RE-CLOSABLE WOUND DRESSING

(71) Applicant: Geof Clippert, St Charles, IL (US)

(72) Inventor: Geof Clippert, St Charles, IL (US)

( * ) Notice: Subject to any disclaimer, the term of this patent is extended or adjusted under 35 U.S.C. 154(b) by 462 days.

This patent is subject to a terminal disclaimer.

(21) Appl. No.: 17/316,071

(22) Filed: May 10, 2021

(65) Prior Publication Data

US 2021/0267808 A1    Sep. 2, 2021

Related U.S. Application Data

(63) Continuation of application No. 16/960,860, filed as application No. PCT/US2019/069168 on Dec. 31, 2019, now Pat. No. 11,000,419.

(60) Provisional application No. 62/865,681, filed on Jun. 24, 2019, provisional application No. 62/865,753, filed on Jun. 24, 2019, provisional application No. 62/865,657, filed on Jun. 24, 2019, provisional application No. 62/786,943, filed on Dec. 31, 2018, provisional application No. 62/786,975, filed on Dec. 31, 2018.

(51) Int. Cl.
| | | |
|---|---|---|
| *A61F 13/00* | (2006.01) | |
| *A61F 13/0246* | (2024.01) | |
| *A61L 15/24* | (2006.01) | |
| *A61L 15/58* | (2006.01) | |

(52) U.S. Cl.
CPC .......... *A61F 13/0253* (2013.01); *A61L 15/24* (2013.01); *A61L 15/58* (2013.01)

(58) Field of Classification Search
None
See application file for complete search history.

(56) References Cited

U.S. PATENT DOCUMENTS

| | | | |
|---|---|---|---|
| 4,324,237 A | 4/1982 | Buttaravoli | |
| 4,399,816 A | 8/1983 | Spangler | |
| 4,641,643 A | 2/1987 | Greer | |
| 4,732,146 A | 3/1988 | Fasline et al. | |
| 4,795,435 A | 1/1989 | Steer | |
| 4,884,563 A | 12/1989 | Sessions | |
| 4,890,608 A | 1/1990 | Steer | |

(Continued)

FOREIGN PATENT DOCUMENTS

| | | |
|---|---|---|
| CN | 103860329 A | 6/2014 |
| GB | 2531612 A | 4/2016 |

(Continued)

OTHER PUBLICATIONS

International Search Report and Written opinion of PCT/US2020/039448; dated Sep. 28, 2020.

(Continued)

*Primary Examiner* — Kim M Lewis

(57) ABSTRACT

A re-closable wound dressing is provided. A base layer is operable to be attached to a skin of a patient. The base layer forms a pre-fabricated aperture through which a wound of the patient is accessible. A cover layer is coupled with the base layer. The cover layer is operable to cover the pre-fabricated aperture, and is permanently adhered to the base layer along at least a portion of the cover layer. The base layer and the cover layer are made of like materials.

19 Claims, 10 Drawing Sheets

(56) References Cited

U.S. PATENT DOCUMENTS

| | | | |
|---|---|---|---|
| 5,086,763 A | 2/1992 | Hathman | |
| 5,244,523 A | 9/1993 | Tollini | |
| 5,449,340 A * | 9/1995 | Tollini | A61M 25/02 |
| | | | 602/57 |
| 5,562,107 A | 10/1996 | Lavender et al. | |
| 5,637,080 A * | 6/1997 | Geng | A61F 13/023 |
| | | | 602/42 |
| 5,702,356 A * | 12/1997 | Hathman | A61F 13/0206 |
| | | | 602/41 |
| 5,722,943 A | 3/1998 | Sessions | |
| 7,118,545 B2 | 10/2006 | Boyde | |
| 8,591,447 B2 | 11/2013 | DiGrazia | |
| 11,000,419 B2 * | 5/2021 | Clippert | A61L 15/26 |
| 11,154,426 B2 * | 10/2021 | Riesinger | A61F 13/00068 |
| 11,197,753 B2 * | 12/2021 | Scruggs | A61F 2/24 |
| 2002/0019602 A1 | 2/2002 | Geng | |
| 2002/0040202 A1 | 4/2002 | Levin | |
| 2007/0282236 A1 | 12/2007 | LaGreca | |
| 2008/0119802 A1 | 5/2008 | Riesinger | |
| 2008/0283426 A1 | 11/2008 | Primer et al. | |
| 2009/0062710 A1 | 3/2009 | Lin | |
| 2011/0015557 A1 | 1/2011 | Aali et al. | |
| 2011/0171277 A1 | 7/2011 | Schönberger | |
| 2016/0067102 A1 | 3/2016 | Cotton | |
| 2016/0135998 A1 | 5/2016 | Riesinger | |
| 2016/0193452 A1 | 7/2016 | Hanson et al. | |
| 2017/0065458 A1 | 3/2017 | Mumby et al. | |
| 2017/0143553 A1 | 5/2017 | Bogue et al. | |
| 2018/0161543 A1 | 6/2018 | Burkholz | |
| 2019/0083322 A1 | 3/2019 | Huang et al. | |

FOREIGN PATENT DOCUMENTS

| | | |
|---|---|---|
| WO | 9504511 A1 | 2/1995 |
| WO | 2011135287 A1 | 11/2011 |
| WO | 2018170122 A1 | 9/2018 |

OTHER PUBLICATIONS

International Search Report and Written opinion of PCT/US2019/069168; dated Mar. 17, 2020.
European Extended Search Report of EP 19908005.2; dated May 19, 2022.

* cited by examiner

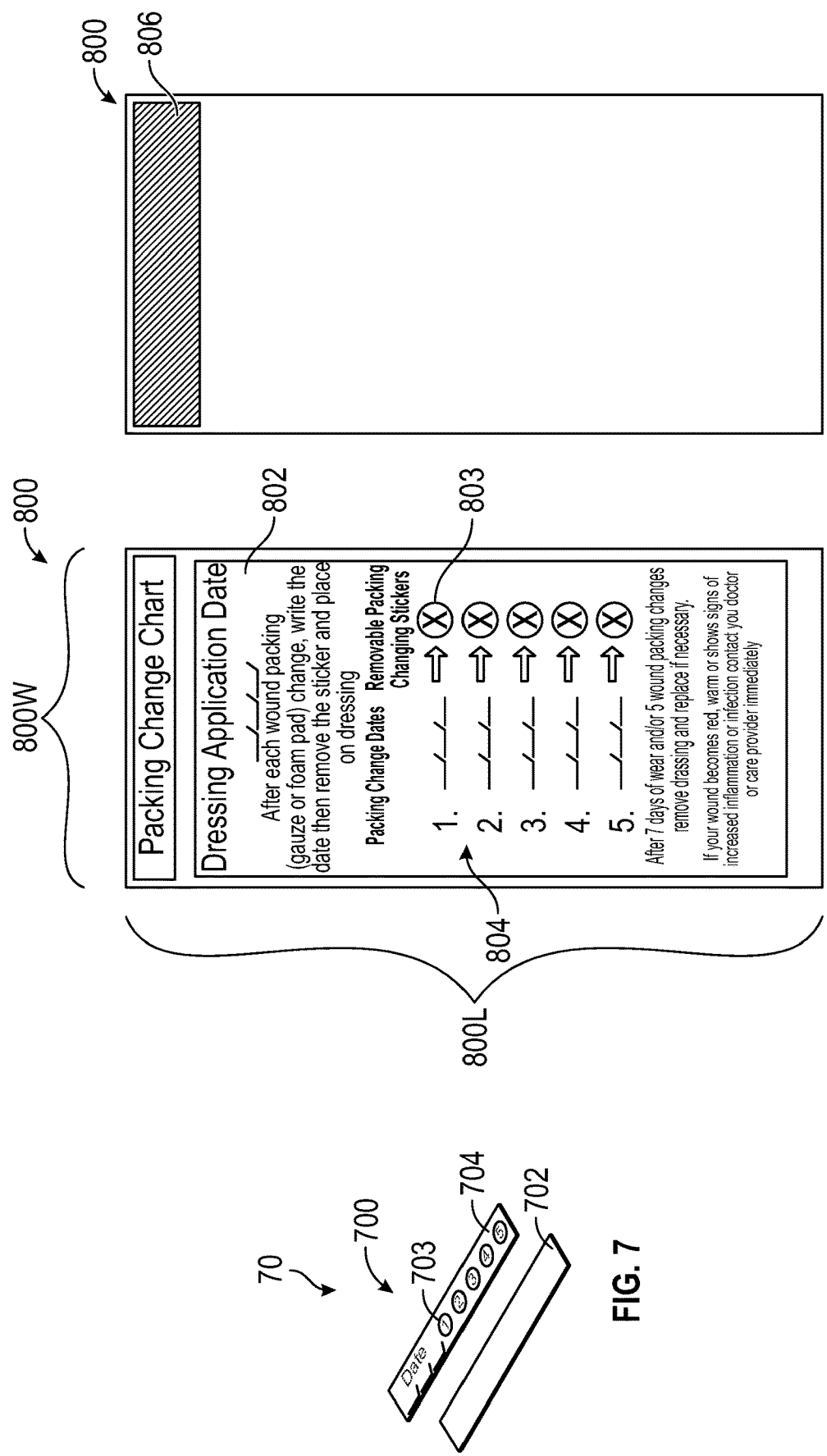

RE-CLOSABLE WOUND DRESSING

CROSS-REFERENCE TO RELATED APPLICATIONS

This application is a continuation of U.S. application Ser. No. 16/960,860, filed on Jul. 8, 2020, a national phase application of PCT/US2019/06918 filed Dec. 31, 2019, claims benefit to U.S. Provisional Patent Application No. 62/786,943, filed in the U.S. Patent and Trademark Office on Dec. 31, 2018, U.S. Provisional Patent Application No. 62/786,975, filed in the U.S. Patent and Trademark Office on Dec. 31, 2018, U.S. Provisional Patent Application No. 62/865,657, filed in the U.S. Patent and Trademark Office on Jun. 24, 2019, U.S. Provisional Patent Application No. 62/865,681, filed in the U.S. Patent and Trademark Office on Jun. 24, 2019, and U.S. Provisional Patent Application No. 62/865,753, filed in the U.S. Patent and Trademark Office on Jun. 24, 2019, each of which is incorporated herein by reference in its entirety for all purposes.

BACKGROUND

Wound dressings cover wounds to prevent infection from the external environment. Wound dressings create a barrier between the clean and sterilized wound and bacteria, moisture, and/or particles in the external environment. Accordingly, the wound is able to fully heal without complication.

BRIEF DESCRIPTION OF THE DRAWINGS

FIGS. 7, 8A, and 8B are examples of diagrams of a date and dressing change management system of a re-closable wound dressing;

DETAILED DESCRIPTION

Figure 1:
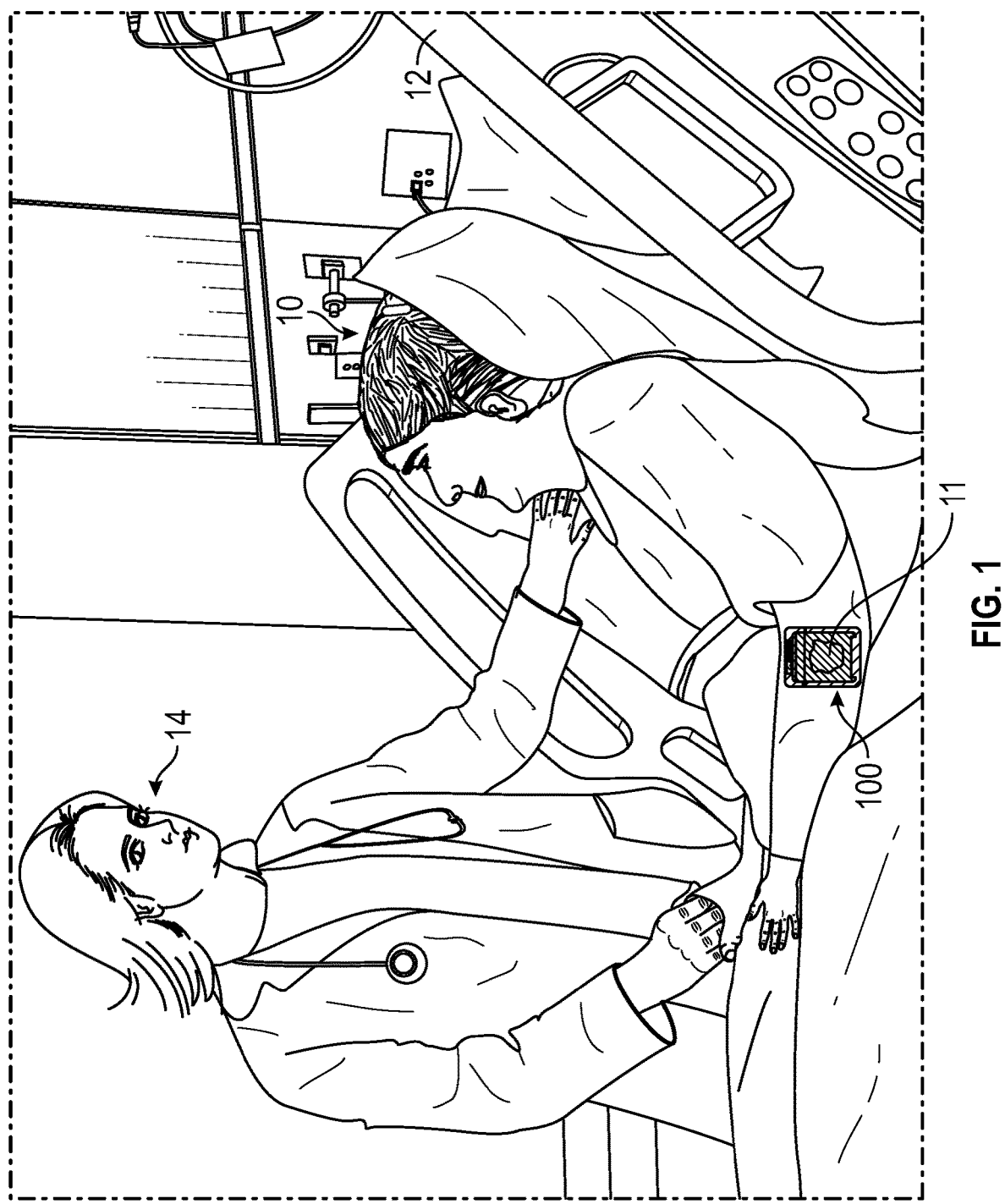
FIG. 1 is a diagram of an example environment in which a re-closable wound dressing can be utilized.

Wounds can pose a significant risk for secondary infections and therefore are treated by covering the wound with a dressing material to absorb wound exudate, reduce pain, and prevent bacterial proliferation. Conventionally, adhesive-backed tapes or films are used in conjunction with foam and non-foam dressings of many different materials. These films and/or tapes are applied over the wound and any additional dressing materials and are adhesively secured to the skin surfaces surrounding the wound. In some scenarios, the conventional foam and/or non-foam pads that cover the wound can be changed by cutting the film dressing around them with a straight blade or other cutting instruments leaving the perimeter of the dressing still attached to the patient's skin. The foam or non-foam padding is then replaced, and additional film dressings are layered on top of the original film dressings to establish a tight seal. If negative pressure wound therapy (NPWT) is being used, a hole is cut in the freshly applied film dressing and a high-pressure tube is placed in or over this hole and secured in place by an adhesive pad which the tubing runs through.

However, by conventional practice, a sharp cutting instrument must be used to cut the dressing off the patient. The additional step of using a sharp cutting instrument can add risk of further injury to the patient and caregiver. Another concern is that layering additional film on top of the primary film can cause a reduction of the dressing's Water Vapor Transmission Rate (WVTR) which directly regulates the moisture microenvironment of wound healing. A significant reduction of a dressing's WVTR can greatly affect the skin's ability to breathe which in turn poses additional risks such as maceration of the tissue surrounding the wound as well as trapping excessive moisture in the dressing which can lead to poor healing of the wound itself.

The wounds may require daily or hourly access for drainage, visual inspection, changing of the foam or non-foam packing, and/or other reasons such as dressing changes for negative pressure applications. To access the wound, the adhesive film or tape is conventionally removed from the skin in order to expose the wound. The repeated removal and/or stripping of these adhesive films and/or tapes to access the wound can cause slight to very severe skin irritation including complete tearing and stripping of the skin especially in the case of an elderly or very sick patient.

Conventionally, the wound sites must be re-dressed upon every access and a new dressing must be applied to cover the wound to promote healing and to protect the wound from infection. The removal and the re-dressing process often require daily visits from a home health provider and is a very time-consuming process that must be done with great attention to the outer edges of the wound as to avoid additional collateral damage to the skin surrounding the wound. These dressing changes can be very costly and contribute to the continued rising costs in health care. Additionally, given cost concerns and discomfort associated with the removal of these conventional film dressings, there is an elevated tendency to prolong the periods between these dressing changes and therefore raise the risks for secondary infections due to the standard of care being compromised.

Disclosed herein is a re-closable wound dressing including a base layer operable to be attached to a skin of a patient. The base layer forms a pre-fabricated aperture through which a wound of the patient is accessible. Accordingly, the aperture does not need to be cut out of the base layer of the dressing by the patient or the caregiver prior to adhering the device to the wound, as the wound dressing already includes the aperture when received by the patient and/or caregiver. A pre-fabricated aperture in the base layer reduces the risk of injury to both patient and caregiver due to the introduction of a sharp knife or blade used in conventional practice for creating the opening.

A cover layer is coupled with the base layer and is operable to overlay the pre-fabricated aperture. The cover layer can have a plurality of sides creating a first portion and a second portion. The first portion can include at least one of the plurality of sides of the cover layer which is operable to be permanently adhered to the base layer to prevent, during normal operation, the cover layer from being separated from the base layer. The second portion can include two or more of the plurality of sides of the cover layer which are operable to be removably coupled with the base layer. Normal operation involves the opening and closing of the cover layer on the base layer. In one example, one side of the cover layer, acting as a hinge, is permanently adhered to the base layer to prevent the one of the plurality of sides from being separated from the base layer. In another example, one side of the cover layer is co-molded with the base layer. In yet another example, one side of the cover layer is vibration welded to the base layer. The description references the permanently adhered construction, but the present disclosure can include any of the above. In at least one example, in describing the connection as being permanently adhered, a scenario is described wherein the force required to remove the permanently adhered portion from the base layer can be at least twice as much force as is required for removing the removably coupled portions from the base layer. In yet another example, the connection described as being permanently adhered can refer to a scenario where the force required to remove the permanently adhered portion from the base layer can be the over ten times greater than the force required for removing the removably coupled portions from the base layer. One side being adhered to the base layer provides ease of adhering and aligning the rest of the cover layer with the base layer, for example without wrinkles and/or contact of adhesive with the wound exposed through the pre-fabricated aperture. The cover layer can be repeatedly lifted to expose the wound and replaced on the base layer to create a seal to protect the wound.

In at least one example, the base layer and the cover layer can be made of materials that are substantially alike. For example the materials can have substantially similar flexibility and/or stretch properties. However, the materials need not be made of the same type of material. In at least one example, the materials of the cover layer and base layer can include three types of films and two types of adhesives.

The base layer can include a landing zone, extending between an edge of the pre-fabricated aperture, surrounding the pre-fabricated aperture, and a predetermined distance towards an outermost edge of the base layer. The landing zone is the preferred zone where the cover layer is to be affixed to the base layer. The cover layer has a perimeter which is greater than a perimeter of the pre-fabricated aperture, so the wound is not exposed when the cover layer is placed on the base layer. When the cover layer is placed on the base layer, the perimeter of the cover layer is disposed in the landing zone. In some examples, the landing zone can span a distance of about 20% to about 65% of the distance from the pre-fabricated aperture to the outermost edge of the base layer. In some examples, the landing zone can span a distance of about 50% of the distance from the pre-fabricated aperture to the outermost edge of the base layer.

The ability for repetitive lifting and the replacement of the cover layer to the predetermined landing zone engineered on the base layer provides consistent and satisfactory margins between all edges of the base film and the liftable edges, which can include one or more lift tabs, of the cover layer. Due to the very thin and fragile characteristics of these films the manual cutting process that is required on previous designs heightens the chances for uneven edges and tearing of the film during the manual cutting process. Conventionally, the manual cutting of the access window creates inconsistent and inadequate margins between the adhesive edges of the cover layer and the manually cut edges of the base layer resulting in misalignment of the cover layer and the base layer. The imprecise alignment and positioning of the edges of the conventional cover layer to the inconsistent edges of the base layer can compromise the effectiveness of the wound dressing. The conventional wound dressing is then unlikely to maintain a 100% closed off barrier to the wound, rendering the conventional wound dressing clinically questionable.

Additionally, as described above, the base layer and the cover layer can be made of like materials in that the flexibility and stretch of the materials are substantially similar. Furthermore, the cover layer can include a top film and an inner film. When included, the inner film adds rigidity to the cover layer. The top film and inner film can be made of like materials as well. In at least one example, the inner film can be a different material than the top film, but share similar properties with the top film. In at least one example, the top film spans the entirety of the cover layer and the inner film covers only a portion of the cover layer. The inner film can be designed such that the inner film is only a border around the area of the cover layer that overlays the pre-fabricated aperture of the base layer. When the inner film only forms the border as described, the rigidity of the cover layer can be increased in the area that includes adhesives designed to releasable couple with the base layer.

Unlike conventional designs that relied on the use of dissimilar materials for these layers, the re-closable wound dressing relies on similar materials in both the films and adhesives that are used in construction. The present re-closable wound dressing implements specialized acrylic and silicone gel adhesives that allow for bonding of the layers as well as the ability to remove the cover layer from the base layer. In one example the silicone gel adhesive is used for the removable adhesive and the acrylic adhesive is used for the permanent adhesive. The bond formed between the base layer and the cover layer can be highly tacky yet flexible. In at least one example, the bond can such that the cover layer and the base layer allow for up to fifty cycles of lifting and replacement of the cover layer from the base layer, which is attached to the patient. In one example, the top film can be a flexible film such as polyethylene (PE).

Conventional wound covers relied on the use of at most one type of adhesive and required the use of dissimilar materials to be used to form the base layer and the cover layer in order to form the boundaries between the base layer and the cover layer. The reliance and use of non-stretchable, dissimilar materials, such as those used in conventional wound covers, did not allow for the independent layers to move in unison during normal movement of the skin and therefore encouraged these layers to pull on one another and the underlying skin. This is not only uncomfortable to the user but also encourages unwanted separation of the layers up to and including the premature opening and separation of the top layer from the base layer. The present design's use of specific adhesives to perform specific requirements allows for the use of flexible and stretchable materials that move in harmony with the skin and therefore are critical features. The materials chosen for the presently disclosed wound dressing allow for the device to remain effective for a period of 7 days of continuous wear even during everyday movement of the skin due to the likeness of the materials. As stated above, the phrase likeness of the materials can be used to indicate that the materials have one or more similar proprieties including, but not limited to, flexibility, stretch, and/or elasticity.

The silicone adhesives can provide a vapor-tight seal even in a moist environment which often provides the best opportunity for healing provided that the environment is kept free of unwanted bacteria. The unique combination of acrylic adhesives and the silicone adhesives that are used to create the desired bond between the cover layer and the base layer reduce the peel force, which is the force required to separate the cover layer from the base layer yet bond the base layer to the underside of the cover layer and also form a flexible border for the cover layer. The reduction in peel force allow for repetitive openings and closings of the cover layer without a risk of the base layer being compromised by tearing or losing its adhesion to the skin which ultimately would cause the wound dressing to fail.

The re-closable wound dressing can be employed in an exemplary environment shown, for example, in FIG. 1. FIG. 1 illustrates a patient 10 lying in a bed 12, for example a hospital bed. The patient 10 has suffered a wound 11 which needs tending and frequent access. While FIG. 1 illustrates the wound 11 as located on the arm of the patient 10, it should be understood that this was done for illustrative purposes and that the wound dressing 100 can be used with a wound 11 located at any area on the patient's 10 body. Additionally, it should be recognized that the size of the wound 11 as illustrated in FIG. 1 is intended as illustrative, and that the wound dressing 100 can be sized to fit wounds of various sizes and shapes without departing from the present disclosure.

The wound 11 is covered and protected by a re-closable wound dressing 100. As will be discussed in greater detail with respect to FIG. 2, the cover layer 106 of the wound dressing 100 can be lifted to access the wound 11, for example by a medical professional 14, without removing a base layer of the wound dressing 100 adhered to the skin of the patient 10. Accordingly, the skin is not irritated by constant removal of adhesive layers. The wound dressing 100 protects the wound 11 from the external environment and ensures a clean space for the wound 11 to heal.

Figure 2A:
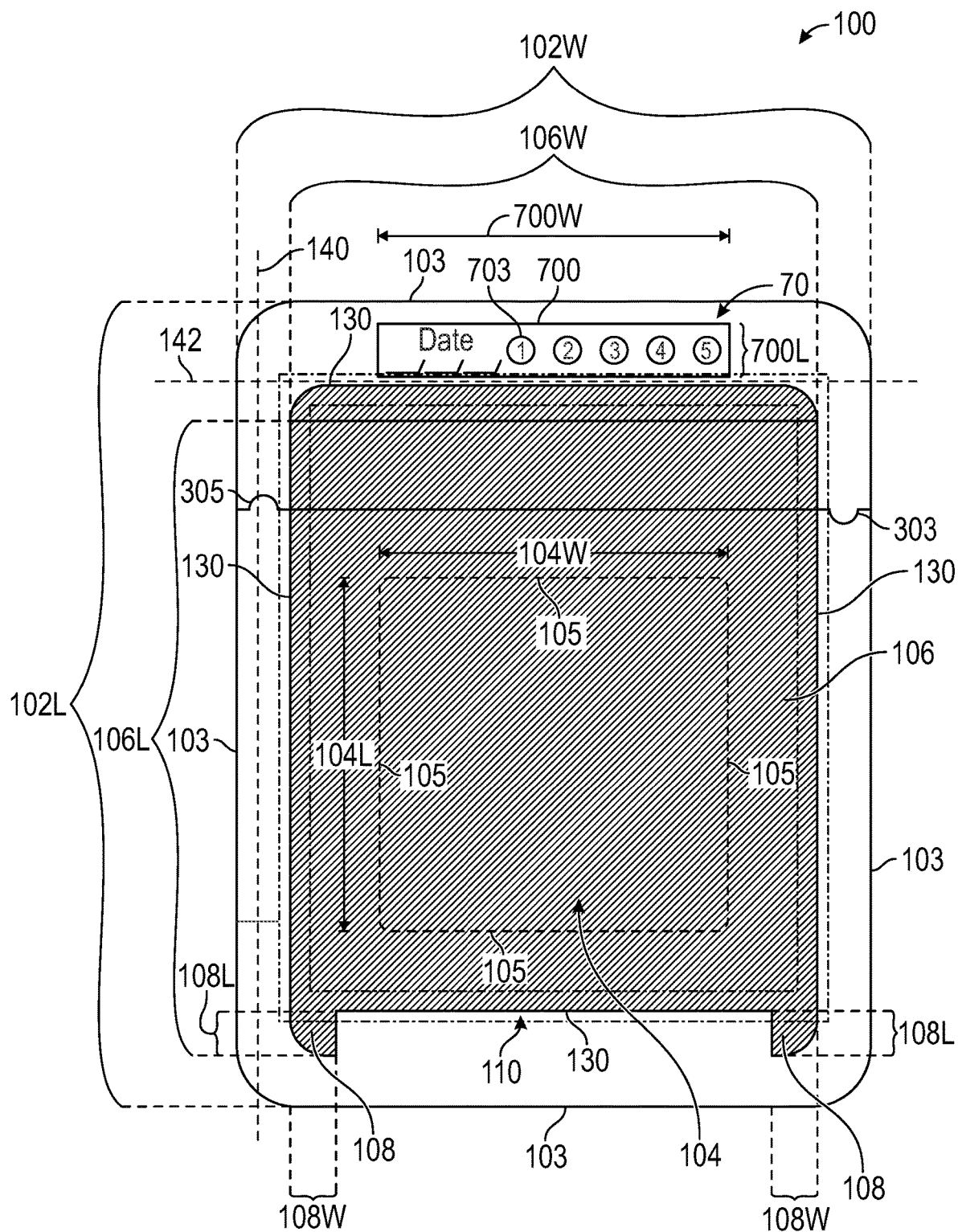
FIG. 2A is an example of a diagram of a re-closable wound dressing in a closed configuration.
Figure 2B:
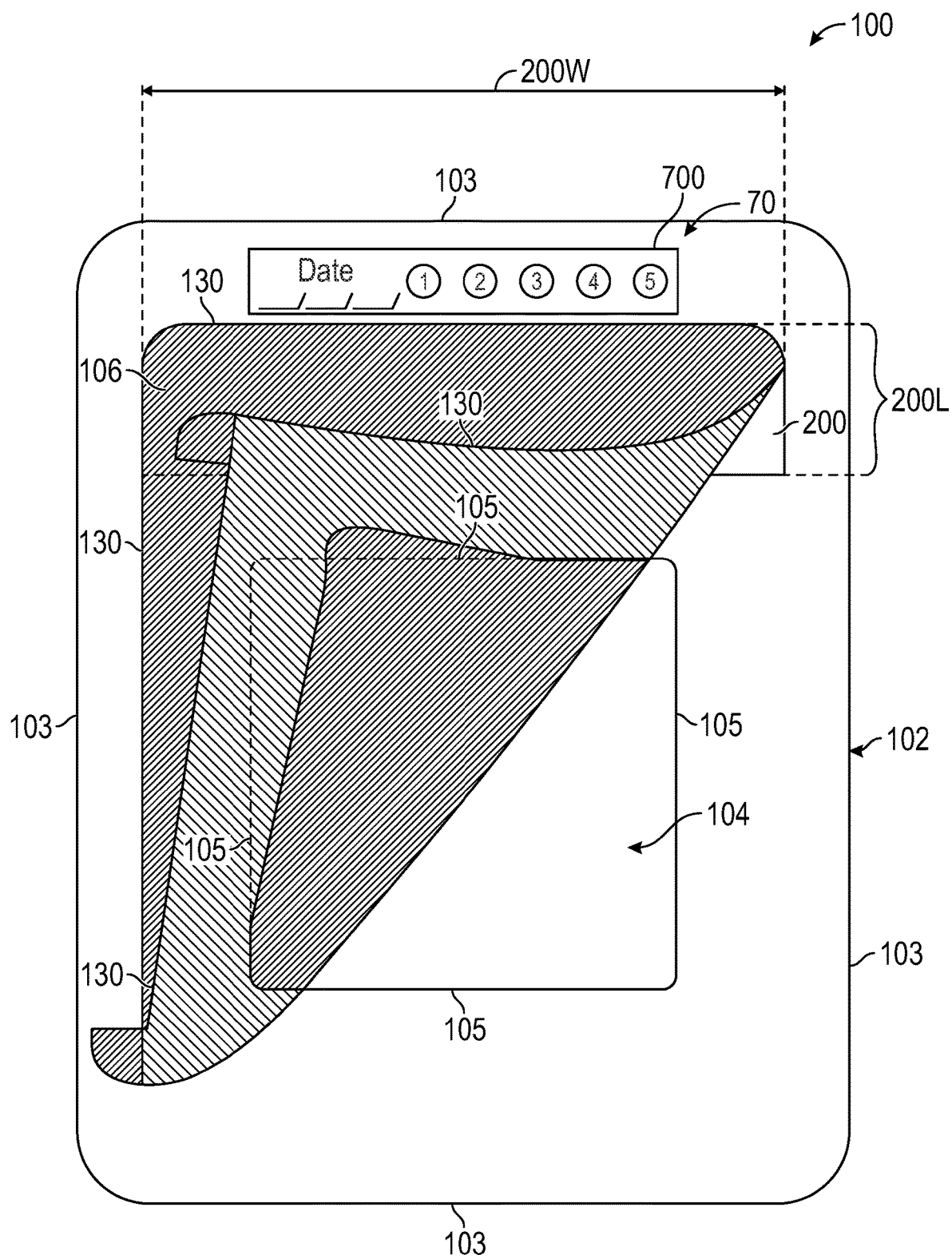
FIG. 2B is an example of a diagram of the re-closable wound dressing of FIG. 2A in a partially open configuration.

FIGS. 2A and 2B are diagrams of a re-closable wound dressing 100. The wound dressing 100 includes a base layer 102 which is operable to be coupled with a patient's skin. For example, the base layer 102 can be coupled with a patient's skin by an adhesive layer. As illustrated in FIG. 2A, the base layer 102 has a substantially rectangular shape. The base layer 102 has a width 102W and a length 102L formed by edges 103 of the base layer 102. In at least one example, the base layer 102 can have a width 102W of about 18 centimeters and a length 102L of about 22 centimeters. As used herein, length (illustrated by dashed line 140) refers to a direction that is perpendicular to the one of the sides 130 of the cover layer 106 that is permanently adhered to the base layer 102. Width (illustrated by dashed line 142) refers to a direction that is parallel to one of the sides 130 of the cover layer 106 that is permanently adhered to the base layer 102. In other examples, the shape of the base layer 102 may be a square, a circle, an oval, a triangle, a hexagon, or any other suitable shape that allows the wound can be covered and accessed.

The base layer 102 forms a pre-fabricated aperture 104 through which the wound of the patient is accessible. By having a pre-fabricated aperture 104, a window does not need to be manually cut out of the base layer 102 of the wound dressing 100 which ensures consistent size and edges and promotes safety. Also, the pre-fabricated aperture 104 prevents manually cut windows to be incorrectly sized and/or shaped so that adhesives from the base layer 102 do not stick to the wound or be too close to the wound. Additionally, the pre-fabricated aperture 104 allows the medical professional applying the wound dressing 100 to visualize the wound during the initial sizing and placement of the wound dressing 100. By being able to visualize the wound, unwanted waste due to incorrect sizing and failed attempts to cut the window can be diminished, as there would not be incorrectly cut wound dressings that would need to be discarded.

As illustrated in FIG. 2A, the pre-fabricated aperture 104 is the shape of a square in that the width 104W and the length 104L of the pre-fabricated aperture 104 are the same. In at least one example, the width 104W of the pre-fabricated aperture 104 is about 10 centimeters, and the length 104L of the pre-fabricated aperture 104 is about 10 centimeters. In other examples, the width 104W and the length 104L of the pre-fabricated aperture 104 may not be the same, such that the pre-fabricated aperture 104 is in the shape of a rectangle. In other examples, the shape of the pre-fabricated aperture 104 may be a circle, an oval, a triangle, a hexagon, or any other suitable shape such that the wound can be accessed. In yet other examples, the shape of the pre-fabricated aperture 104 can be sized so that it matches with available sizes for gauze pads or other dressings. For example, gauze pads can be sized, among others, to be four inches by four inches, three inches by three inches, and two inches by two inches. Therefore, the present pre-fabricated aperture 104 can be sized accordingly. The other components of the presently described apparatus can be scaled accordingly.

A cover layer 106 operable to overlay the pre-fabricated aperture 104 such that the wound is protected from the external environment and is coupled with the base layer 102 using adhesives. The cover layer 106 has a plurality of sides 130 which forms a perimeter. The perimeter of the cover layer 106 is larger than a perimeter of the pre-fabricated aperture 104 which is formed by a plurality of edges 105 such that the cover layer 106 can cover the pre-fabricated aperture 104. As illustrated in FIG. 2A, the cover layer 106 has a substantially rectangular shape. The cover layer 106 has a width 106W and a length 106L formed by the plurality of sides 130. In at least one example, the cover layer 106 can have a width 106W of about 15 centimeters and a length 106L of about 18 centimeters. In other examples, the shape of the cover layer 106 may be a square, a circle, an oval, a triangle, a hexagon, or any other suitable shape such that the pre-fabricated aperture 104 and the wound can be covered and accessed. In other examples, the size of the cover layer 106 can be between 50 percent and 70 percent larger than the pre-fabricated aperture 104.

In at least one example, the cover layer 106 is substantially transparent such that the wound can be visually seen through the cover layer 106 without needing to remove the cover layer 106. Accordingly, the wound would not be unnecessarily exposed to bacteria and other pathogens in the external environment. In some examples, the cover layer 106 may be waterproof such that the wound is not exposed to excessive moisture. In other examples, the cover layer 106 can be translucent or opaque. When the cover layer 106 is translucent, it can still be possible to monitor the wound without removing the cover layer.

The base layer 102 includes a landing zone 110 which is shown in FIG. 2A as an area within dash-dot lines. The landing zone 110 surrounds the pre-fabricated aperture 104 and extends between a distance formed by an outermost edge 103 of the base layer 102 and an edge 105 of the pre-fabricated aperture 104. In some examples, the landing zone 110 is positioned such that the remaining surface area of the base layer 102 on either side of the landing zone 110 is shared equally. In at least one example, the landing zone 110 is about 20% to about 65% of the distance from the pre-fabricated aperture 104 to the outermost edge 103 of the base layer 102. In some examples, the landing zone 110 can be about 40% to about 65% of the distance from the pre-fabricated aperture 104 to the outermost edge 103 of the base layer 102. In some examples, the landing zone 110 can be about 45% to about 55% of the distance from the pre-fabricated aperture 104 to the outermost edge 103 of the base layer 102. In some examples, the landing zone 110 can be about 50% of the distance from the pre-fabricated aperture 104 to the outermost edge 103 of the base layer 102. The plurality of sides 130 of the cover layer 106 are shaped and sized such that the perimeter of the cover layer 106 is disposed in the landing zone 110.

The precise placement of the sides 130 of the cover layer 106 prevents or limits the potential for the separation of the base layer 102 from the skin of the patient while providing a viable seal to prevent the introduction of moisture and bacteria into the wound. By having the perimeter of the cover layer 106 disposed in the landing zone 110, the forces applied to the base layer 102 during the lifting and separation of the re-closable cover layer 106, for example as illustrated in FIG. 2B, are directed away from the edges 103 of the base layer 102. By directing the forces away from the edges 103 of the base layer 102, the potential for the forces when the cover layer 106 is lifted to peel any of the material of the base layer 102 away from the skin is reduced. Additionally, the cover layer 106 being sized to fit within the landing zone 110 guides the sides 130 of the cover layer 106 to seal against the material of the base layer 102 and not against the skin while forming a viable seal to protect the wound from the introduction of unwanted bacteria and moisture.

The skin-friendly properties of the base layer 102 allow the base layer 102 to remain safely secured to the skin surfaces surrounding the wound for long periods of time, for example up to 7 days, while the transparency of the cover layer 106 allows for visual inspection and frequent access to the wound by opening and closing the cover layer 106.

In at least one example, as illustrated in FIGS. 2A and 2B, the cover layer 106 can include at least one lift tab 108 which can extend from one of the plurality of sides 130 of the cover layer 106. The lift tabs 108 can be used to lift the cover layer 106 from and replace the cover layer 106 on the base layer 102. FIG. 2B illustrates the cover layer 106 partially lifted from the base layer 102 to expose a wound through the pre-fabricated aperture 104. In some examples, the lift tabs 108 do not include adhesives so that the lift tabs 108 are easily gripped and pulled away from the base layer 102. In some examples, the lift tabs 108 can have a width 108W of about 1 centimeter and a length 108L of about 1 centimeter. In other examples, the width and length of the lift tabs 108 may not be the same. In other examples, the width and length of the lift tabs 108 can be sized according to the size of the pre-fabricated aperture 104.

As can be seen in FIG. 2B, one of the sides 130 of the cover layer 106 is permanently adhered to the base layer 102 to prevent the one of the plurality of sides 130 from being separated from the base layer 102. For example, a first adhesive region 200 can include an acrylic adhesive that can be used to permanently adhere the one side 130 of the cover layer 106 to the base layer 102 to function as a hinge. The first adhesive region 200 can include a length 200L and a width 200W, the dimensions 200W, 200L of the first adhesive region 200 can be configured such that there is sufficient coupling between the cover layer 106 and the base layer 102. In other examples, other adhesives may be utilized such that the one side 130 of the cover layer 106 is permanently coupled with the base layer 102. Permanently coupled may be defined as difficult to remove or separate without excessive force or effort. The soft and flexible hinging of the cover layer 106 with the base layer 102 by adhesion provides for a hinge-like design without the addition of a hinge element. The strong, permanent adhesion of the one side 130 of the cover layer 106 with the base layer 102 acting as a form of a hinge greatly reduces the potential for the re-closable cover layer 106 to fold on itself during the opening and closing of the cover layer 106. Additionally, as illustrated in FIG. 2B, the hinge like design of the wound dressing 100 allows for only 3 sides or 75% of the cover layer 106 to be lifted from the base layer 102 to access the underlying wound, which can reduce the failure points by a minimum of 25% over conventional designs. Also, the side 130 having a high degree of adhesiveness can dictate the orientation of the re-closable cover layer 106 to the base layer 102. In at least one example, the permanent adhesive side 130 can be positioned such that the orientation of the side 130 is parallel to and precisely abuts the edge of the pre-fabricated aperture 104.

In at least one example, the base layer 102 and the cover layer 106 can be made of like materials which permit the base layer 102 and the cover layer 106 to both move in harmony with the skin and one another as they have similar flexibility, elasticity, bend, stretch, and flex properties. The materials of the base layer 102 and the cover layer 106 allow for the wound dressing 100 to remain effective for a period of 7 days of continuous wear even during everyday movement of the skin due to the likeness of the materials. Additionally, the materials being like materials can reduce or prevent the base layer 102 and the cover layer 106 from flexing or moving in different ways, which can improve comfort to the patient as well as reduce or prevent undesired separation between the base layer 102 and the cover layer 106. In at least one example, the material of the base layer 102 can include polyurethane, and the material of the cover layer 106 can include thermoplastic polyurethane. The similarities of polyurethane and thermoplastic polyurethane define one example of what is required to establish likeness of materials.

In at least one example, the cover layer 106 can include a date and dressing change management system 70 which can allow for notation of at least one of the following: time and/or date of accessing the wound, time and/or date of application of the wound dressing, and/or number of times the wound has been accessed. The date and dressing change management system 70 can include a dressing portion 700 which is disposed on the wound dressing 100 and can have a width 700W of about 10 centimeters and a length 700L of about 1.5 centimeters. In other examples, the width 700W and the length 700L of the dressing portion 700 can vary as desired.

Figure 3:
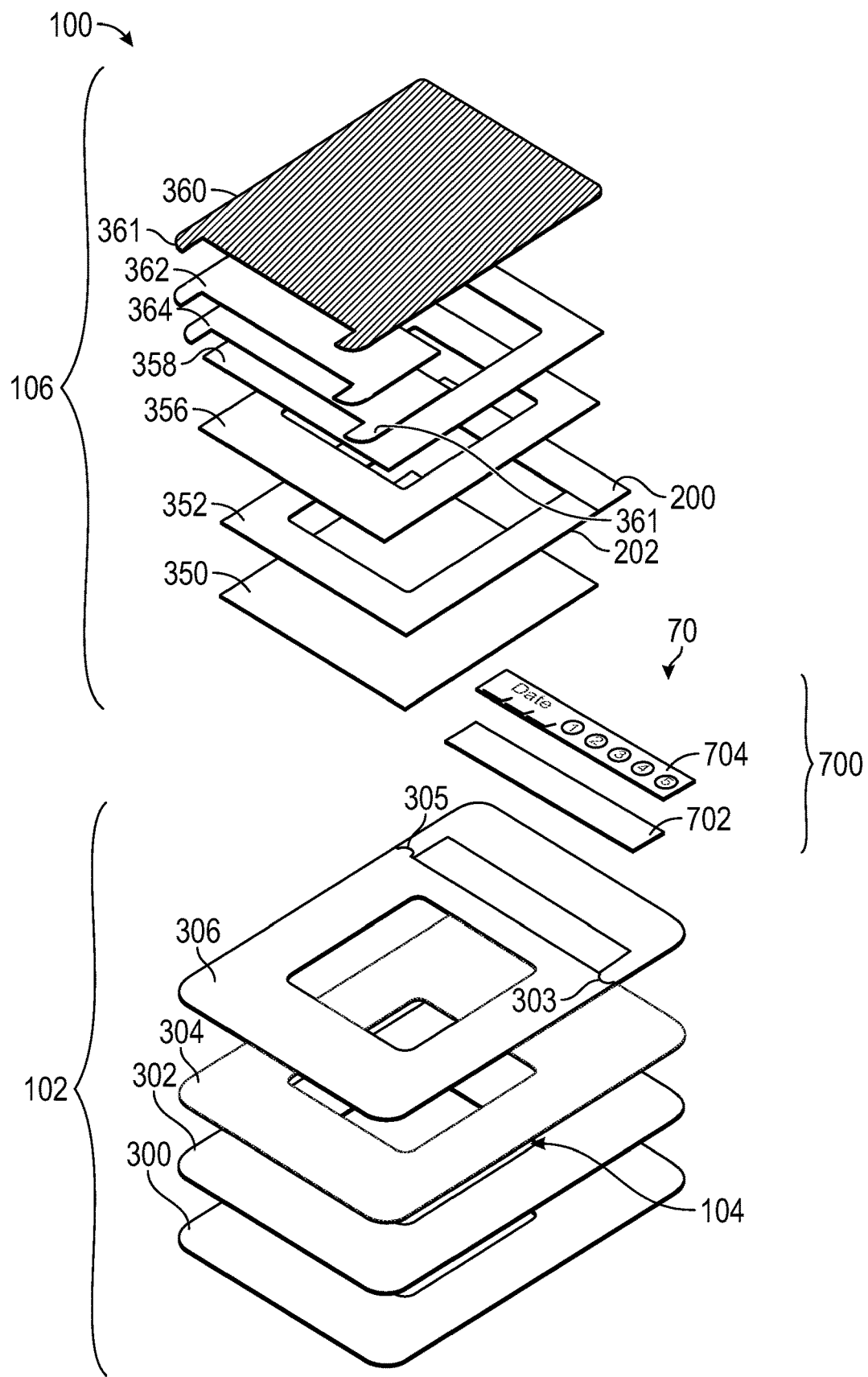
FIG. 3 is an exploded, isometric view of an example of a re-closable wound dressing.

FIG. 3 illustrates an exploded, isometric view of an exemplary wound dressing 100. As discussed above, the wound dressing 100 includes a base layer 102 and a cover layer 106. The base layer 102 can include a base film 304 with an adhesive layer 302 disposed on the underside of the base film 304 such that the base film 304 can be adhered to the skin of a patient. In at least one example, the base film 304 can include polyurethane. In some examples, the base film 304 can be made of any suitable material that is conformable, breathable, and/or waterproof. The base film 304 is a sterile barrier providing a soft, conformable, vapor permeable, waterproof, absorbable, transparent, hypoallergenic, and/or pliable film providing a sterile barrier to external contaminates including liquids, bacteria, and/or viruses. The adhesive layer 302 can include, for example, an acrylic adhesive to provide strong adhesion to the patient's skin without causing irritation. The base film 304 includes a pre-fabricated aperture 104 as discussed above through which a wound can be accessed.

The base layer 102 also can include a date and dressing change management system 70. The date and dressing change management system 70 can include a dressing portion 700 disposed on the wound dressing 100. The dressing portion 700 can include a sticker 704 on which data can be marked such as the date and number of times changed. In at least one example, the sticker 704 can be made of fabric. In other examples, the sticker 704 can be made of plastic, metal, or any other suitable material such that the sticker 704 can be marked by a writing tool. An adhesive 702, such as acrylic adhesive, can be disposed under the sticker 704 to adhere the sticker 704 with the base film 304. Additionally, the date and dressing change management system 70 can include a plurality of packing change stickers 803 that are further illustrated in FIG. 8A. The plurality of packing change stickers 803 can be placed on the dressing portion 700 over indicators 703 numbered 1, 2, 3, 4, and 5, as shown and described in detail below.

In at least one example, as illustrated in FIG. 3, a removable release paper 300 can be disposed against the adhesive layer 302 opposite the base film 304. The removable release paper 300 can protect the strong adhesive properties of the adhesive layer 302 until the wound dressing 100 is to be applied. In at least one example, the removable release paper 300 can be coated with a release agent. In some examples, a second removable release paper 306 can be included above the base film 304 opposite the adhesive layer 302 and between the base layer 102 and the cover layer 106. The second removable release paper 306 can be included to provide stability and maintain cleanliness of the base layer 102 until the wound dressing 100 is applied onto the patient. In one example the second removable release paper 306 can be made to separate into two parts using joints 303, 305.

Prior to application, removable release paper 300 can be removed by peeling the removable release paper 300 away from adhesive layer 302 to ready the application of the wound dressing 100 to the patient's skin. Once the wound dressing 100 has been successfully applied by fixating the base layer 102 to the patient's skin, second removable release paper 306 can be removed thus revealing the base layer 102 as a functional sterile skin barrier surrounding the wound that is centered inside its pre-fabricated aperture 104.

In at least one example, the cover layer 106 includes a top film 360 and an inner film 356. In at least one example, the cover layer 106 can include a tab layer 364. The cover layer 106 can also include two or more adhesive layers. A first adhesive layer 352 or an inner film adhesive layer can be formed on the inner film. The first adhesive layer 352 can include a first adhesive region 200 and a second adhesive region 202. The first adhesive region 200 is operable to be permanently adhered to the base layer 102 to prevent, during normal operation, the cover layer 106 from being separated from the base layer 102. In at least one example, the first adhesive region 200 can function as a hinge when the cover layer 106 is moved relative to the base layer 102. The second adhesive region 202 is configured to be removably coupled with the base layer 102. In at least one example, the first adhesive region 200 is an acrylic adhesive, and the second adhesive region 202 is silicon adhesive.

A second adhesive layer 358 or top film adhesive layer can be adhered to the inner film 356 at a side facing the top film 360. In at least one example, the second adhesive layer 358 can comprise acrylic adhesive. In one example, the top film 360 and the inner film 356 can be adhered to one another via the second adhesive layer 358. As shown, the cover layer can include a tab layer 364 and a tab adhesive layer 362. In at least one example, the tab adhesive layer 362 can comprise an acrylic adhesive. The tab layer 364 is formed such that the tab layer includes one or more lift tabs 361. In at least one example, the tab layer 364 can comprise PE. As illustrated, the tab layer 364 includes two lift tabs 361. The lift tabs 361 allow for easier removal of the cover layer 106 relative to the base layer 102 as the one or more tabs 361 do not include an adhesive on a side nearest the base layer 102. As shown, the top film 360 can also include one or more lift tabs 361. By having the lift tabs 361 formed of more than one layer, the lift tabs 361 can be made such that there is increased strength and rigidity.

For shipment purposes, a removable film 350 can be adhered to the bottom of the second adhesive layer 352. The removable film 350 assures that the second adhesive layer 352 can remain tactile for later use. In at least one example, the removable film 350 can comprise a fluoroplastic film. In additional examples, the cover layer 106 can include any combination of the above described components as desired.

The top film 360 is operable to cover the pre-fabricated aperture 104 of the base layer 102 as well as be repeatedly lifted and replaced onto the base layer 102. In at least one example, the top film 360 is at least partially transparent such that the wound can be seen without lifting the cover layer 106. In another example, the top film 360 is transparent. A material of the top film 360 can include thermoplastic polyurethane. The top film 360 can be a transparent sterile barrier providing antimicrobial properties, breathability, biocompatibility, elasticity, elastomeric memory, chemical resistance, microbial resistance, waterproofness, a comfortable soft feel, tear resistance, and/or puncture resistance. In some examples, the material of the top film 360 can vary, so long as the top film 360 of the cover layer 106 and the base film 102 are made of like materials. The use of flexible and stretchable like materials permit the base layer 102 and the cover layer 106 to both move in harmony with the skin and one another. The materials of the base layer 102 and the cover layer 106 allow for the wound dressing 100 to remain effective for a period of 7 days of continuous wear even during everyday movement of the skin due to the likeness of the materials. Additionally, the likeness of the materials reduce or prevent the base layer 102 and the cover layer 106 from flexing or moving in different ways, which can improve comfort to the patient as well as prevent undesired separation between the base layer 102 and the cover layer 106.

In at least one example, a first adhesive layer 358 can be adhered to the top film 360. The first adhesive layer 358 can include acrylic adhesive to strongly adhere the top film 360 with an inner film 356. The inner film 356 can include a material similar to or the same as the top film 360 and the base layer 102, for example polyurethane or polyethylene, such that the flexibility and harmony of movement of the cover layer 106 and the base layer 102 can be maintained. In at least one example, the inner film 356 can have more rigidity than the top film 360 yet still have flexibility to allow the wound dressing 100 to move substantially in unison with the skin. By moving substantially in unison with the skin, the wound dressing 100 can maintain contact with the skin and maintain a level of comfort to the patient.

The second adhesive layer 352 can be included to attach the cover layer 106 with the base layer 102. The second adhesive layer 352 can be attached to the underside of the inner film 356 opposite the top film 360 and proximate the base layer 102. The second adhesive layer 352 includes one side of a first adhesive region 200 that includes an adhesive, such as acrylic adhesive, to permanently attach one side 130 of the cover layer 106 to the base layer 102 to function as a hinge. In other examples, other adhesives may be utilized such that the one side 130 of the cover layer 106 is permanently coupled with the base layer 102. The soft and flexible hinging of the cover layer 106 with the base layer 102 by adhesion provides for a hinge like design. The second adhesive layer 352 can be hypoallergenic and/or safe for contact with the skin.

The rest of the second adhesive layer 352 can include an adhesive of light to moderate tack, such as silicone adhesive, such that the second adhesive region 202 of the cover layer 106 can be removably attached to, but also easily lifted from, the base layer 102. Accordingly, a portion of the cover layer 106 can be lifted from the base layer 102 to expose the wound without removing or adjusting the base layer 102. Each of the adhesives discussed herein are able to function in the presence of moisture. In at least one example, the second adhesive layer 352 is capable of being peeled apart if the cover layer 106 were to fold such that the second adhesive layer 352 adhered to itself or other portions of the cover layer 106.

In some examples, the second adhesive region 202 can form a tacky yet flexible bond between the base layer 102 and the cover layer 106 capable of up to 50 cycles of lifting and replacement of the cover layer 106 to the base layer 102.

As illustrated in FIG. 3, each of the first adhesive layer 358, the inner film 356, and the second adhesive layer 352 can form an aperture corresponding to the pre-fabricated aperture 104 of the base layer 102. Accordingly, the adhesive layers 358, 352 do not interfere with or make contact with the wound exposed through the pre-fabricated aperture 104.

Figure 4:
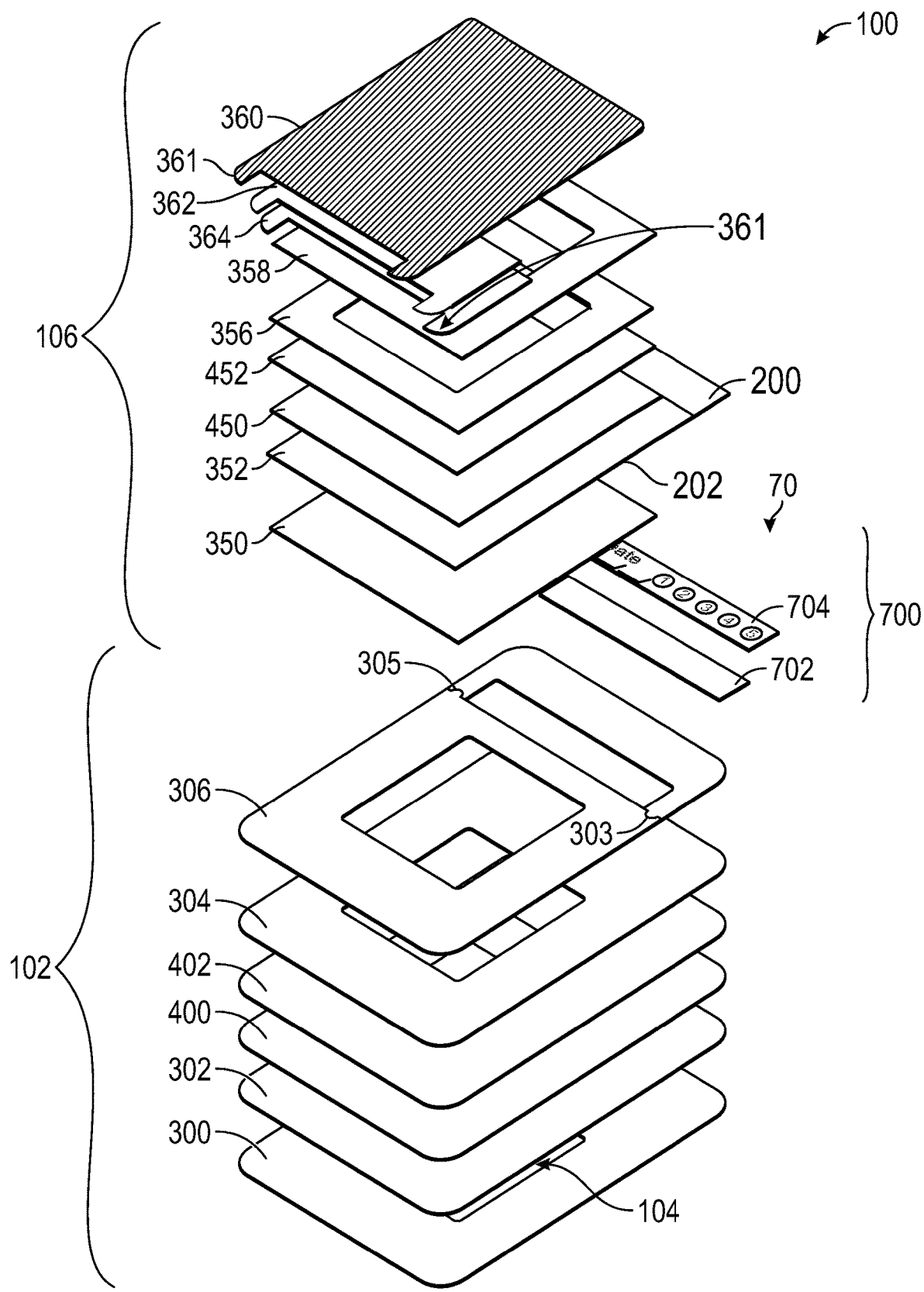
FIG. 4 is an exploded, isometric view of another example of a re-closable wound dressing.

FIG. 4 illustrates a wound dressing 100 which can include each of the features discussed above in FIG. 3, but further including a thermo-reactive and/or hydro-reactive properties.

In at least one example, thermo-reactive properties can be included using thermo-reactive ink 452 in the cover layer 106 and/or by thermo-reactive ink 402 in the base layer 102. Thermo-reactive ink 452, 402 can be any ink which changes states when in the presence of a specific range of temperature. For example, the thermo-reactive ink 452, 402 can change color when exposed to a range of temperature, for example average skin temperature of about 91 degrees Fahrenheit or 33 degrees Celsius±5%. In at least one example, the thermo-reactive ink 452, 402 can indicate whether an infection is present or beginning to form. For example, the thermo-reactive ink 452, 402 may change colors or provide different patterns depending on the range of temperature such that the thermo-reactive ink 452, 402 functions as a skin thermometer.

In at least one example, thermo-reactive ink 402 can be included in the base layer 102. When exposed to the predetermined range of temperature, the thermo-reactive ink 402 can change states, for example to a specific color, indicating that the base layer 102 is sufficiently coupled with the patient's skin.

In at least one example, thermo-reactive ink 452 can be placed in harmony along at least a portion of, or alternately along all, liftable sides of the cover layer 106 by placing this thermo-reactive ink 452 into, on top of, below, or between the layers that form the less tacky sides intended to be separated and re-attached to the base layer 102. When exposed to the predetermined range of temperature, the thermo-reactive ink 452 can change states, for example to a specific color, indicating that the cover layer 106 has been completely sealed down on the base layer 102. The thermo-reactive ink 452 changing color can be firm indicator that the cover layer 106 has been properly adhered to the base layer 102 because the desired temperature has been reached due to its proximity to the underlying skin when the cover layer 106 is properly closed.

Additionally, the thermo-reactive inks 452, 402 can be used to indicate to the user that wound dressing 100 is no longer viable when the user is unable to obtain or maintain a positive reaction from the thermo-reactive inks 452, 402. The lack of color change is designed to indicate to the user that the wound dressing 100 needs to be removed and replaced because its limits have been reached or exceeded.

In some examples, hydro-reactive ink 450, 400 can be integrated into the wound dressing 100. The hydro-reactive ink 450, 400 can provide feedback when there is a presence of moisture within the wound dressing 100. Hydro-reactive ink 450, 400 may be placed into, on top of, below or between the layers that form the adhesive areas of the cover layer 106 and/or base layer 102. The hydro-reactive inks 450, 400 can change states, for example color, when in the presence of water or moisture. The hydro-reactive inks 450, 400 alert that water or moisture has been introduced into areas of the wound dressing 100 or the underlying skin that are intended to be kept dry and free of water or moisture. In at least one example, the hydro-reactive inks 450, 400 can change to predetermined colors or patterns to indicate the level or range of moisture and/or humidity for the wound dressing 100. For example, the color of the hydro-reactive inks 450, 400 can change to a certain shade of blue which can be compared to a chart to indicate that the level of humidity is 70%. Inclusion of the hydro-reactive inks 450, 400 can limit the potential for skin maceration or break down of the skin resulting from prolonged exposure to moisture. Maceration of skin can lead to secondary fungal and or bacterial infections that can potentially become systemic in nature, requiring more aggressive treatments including antibiotics and antifungals. The prevention and early detection of moisture on the skin being covered by a wound dressing 100 is critical to the prevention of skin maceration especially in longer wear film dressings that can be worn for up to 7 days.

Figure 5:
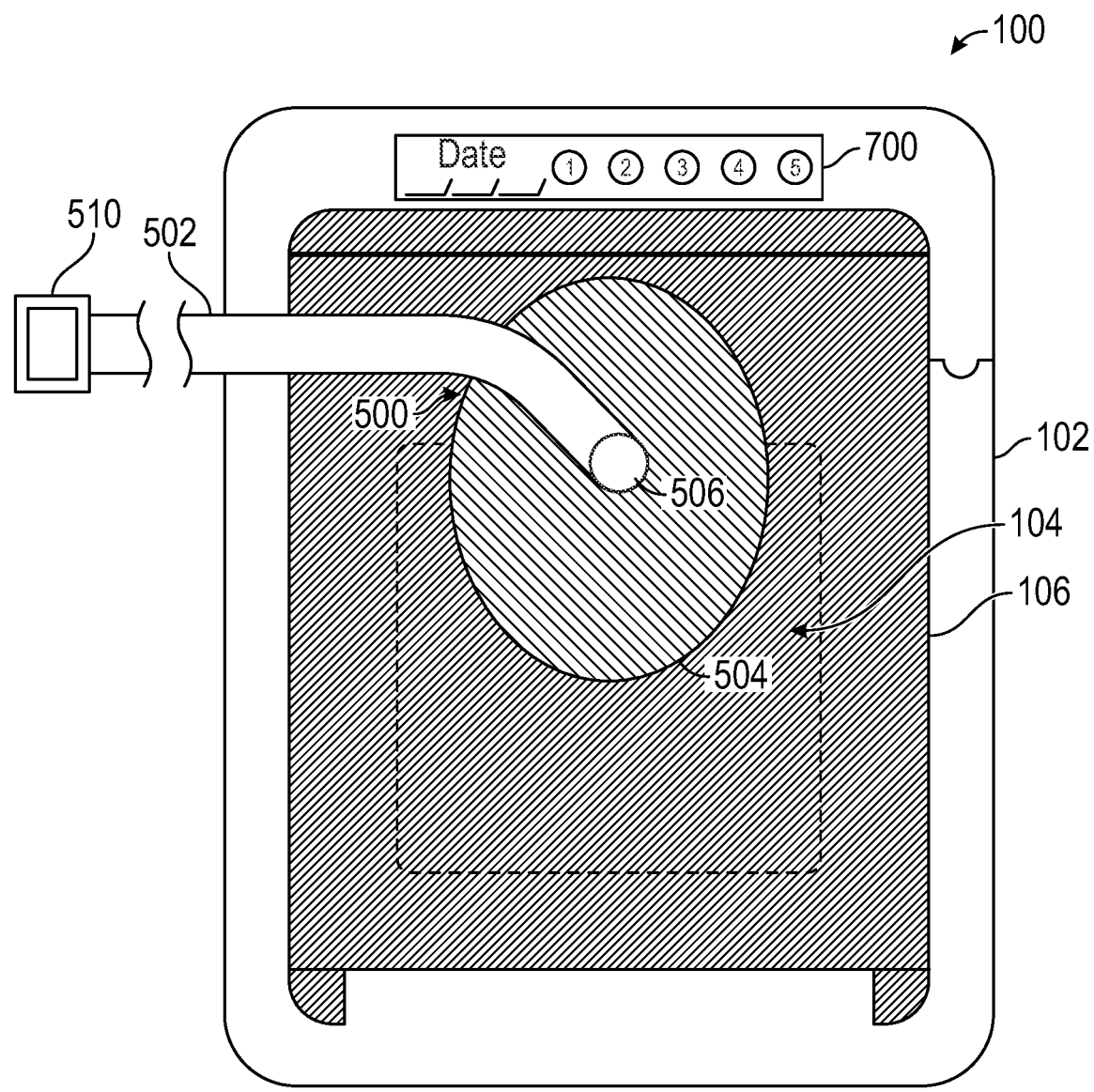
FIG. 5 is a diagram of another example of a re-closable wound dressing.
Figure 6:
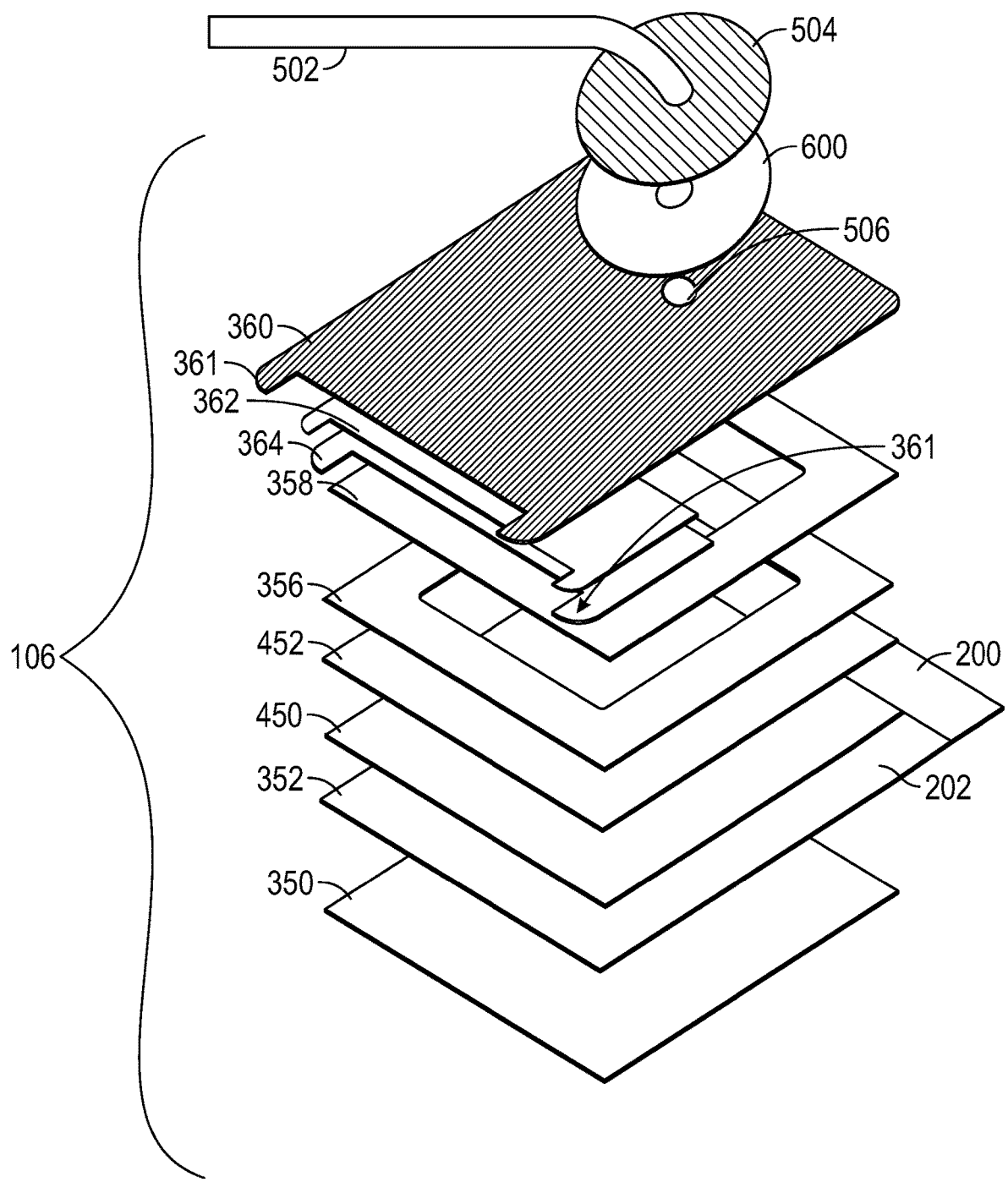
FIG. 6 is an exploded, isometric view of an example of a cover layer of the re-closable wound dressing of FIG. 5.

FIGS. 5 and 6 illustrate a wound dressing 100 which can include each and any of the features discussed above in FIGS. 3 and 4, and can further be utilized in negative pressure wound therapy (NPWT). NPWT can aid in the healing process by removing excess fluid and improve circulation.

The wound dressing 100 illustrated in FIGS. 5 and 6 can include a negative pressure system 500 which can include tubing 502 in fluid communication with the wound through an aperture 506 in the cover layer 106. The tubing 502 can be coupled with a cuff 504 which can be attached to the top film 360 of the cover layer 106 by an adhesive layer 600, as shown in FIG. 6. The adhesive layer 600 can include, for example, acrylic adhesive to provide a strong attachment and seal while maintaining the flexibility of the cover layer 106. The tubing 502 can be fluidly coupled with a pump 510 which apply a vacuum through the sealed wound dressing 100 to enhance circulation and remove wound fluids from the wound area. The tubing 502 and the cuff 504 can be capable of withstanding and maintaining constant or intermittent negative pressures, for example between about −75 mmHg and about −125 mmHg, for NPWT. In at least one example, the wound dressing 100 can be made having the tubing 502 and cuff 504 attached to the cover layer 106. In an alternative example, the wound dressing 100 can include a cover layer 106 having the aperture and the cuff 504 coupled with the cover layer 106, but without a tubing 502. In such instances, suitable tubing 502 operable to couple the cuff 504 can be provided separately by a doctor or health care practitioner.

With the wound dressing 100 as illustrated in FIGS. 5 and 6, caregivers have the flexibility of choosing a foam or packing of their choice depending on the variables of the wound that is being treated. The foams or packings can be inspected and changed quickly without cutting or removing the wound dressing 100 from the skin.

FIGS. 7, 8A, and 8B illustrate a date and dressing change management system 70 which can include notation of at least one of the following: time and/or date of accessing the wound, time and/or date of application of the wound dressing, and/or number of times the wound has been accessed. In at least one example, as illustrated in FIG. 7, the date and dressing change management system 70 can include a dressing portion 700 which can be applied or disposed on the wound dressing 100. The dressing portion 700 can include an adhesive 702 to be applied on the wound dressing 100 as discussed above. The adhesive 702 can be utilized to mark, for example, the date and/or number of times the wound has been accessed, inspected, and/or cleaned. Also, the adhesive 702 can be utilized to note when and/or how many times dressing pads have been changed and/or balms or topical ointments have been applied. In at least one example, the sticker 704 can be made of fabric. In other examples, the sticker 704 can be made of plastic, metal, or any other suitable material such that the sticker 704 can be marked by a writing tool. An adhesive 702, such as acrylic adhesive, can be disposed under the sticker 704 to adhere the sticker 704 with the base film 304. Additionally, packing change stickers 803 can be applied to cover indicators 703.

In at least one example, as illustrated in FIGS. 8A and 8B, the date and dressing change management system 70 can include a packing portion 800. In some examples, the packing portion 800 can contain the wound dressing 100. The packing portion 800 can be used to indicate the dressing application date 802, the packing change dates 804, and/or any information about the use of the wound dressing 100 that is needed. As illustrated in FIG. 8B, the rear of the packing portion 800 can include an adhesive 806, for example acrylic adhesive, such that the packing portion 800 can be attached to a surface such as a wall, a bed, and/or a dresser. In at least one example, the packing portion 800 can have a width 800W of about 12 centimeters and a length 800L of about 15 centimeters. The dimensions 800W, 800L of the packing portion 800 can vary as desired, for example depending on the size and shape of the wound dressing 100 and/or dimensions of the area to be attached. As shipped, the packing portion 800 can include packing change stickers 803 that can be removed and place over indicators 703.

Figure 9:
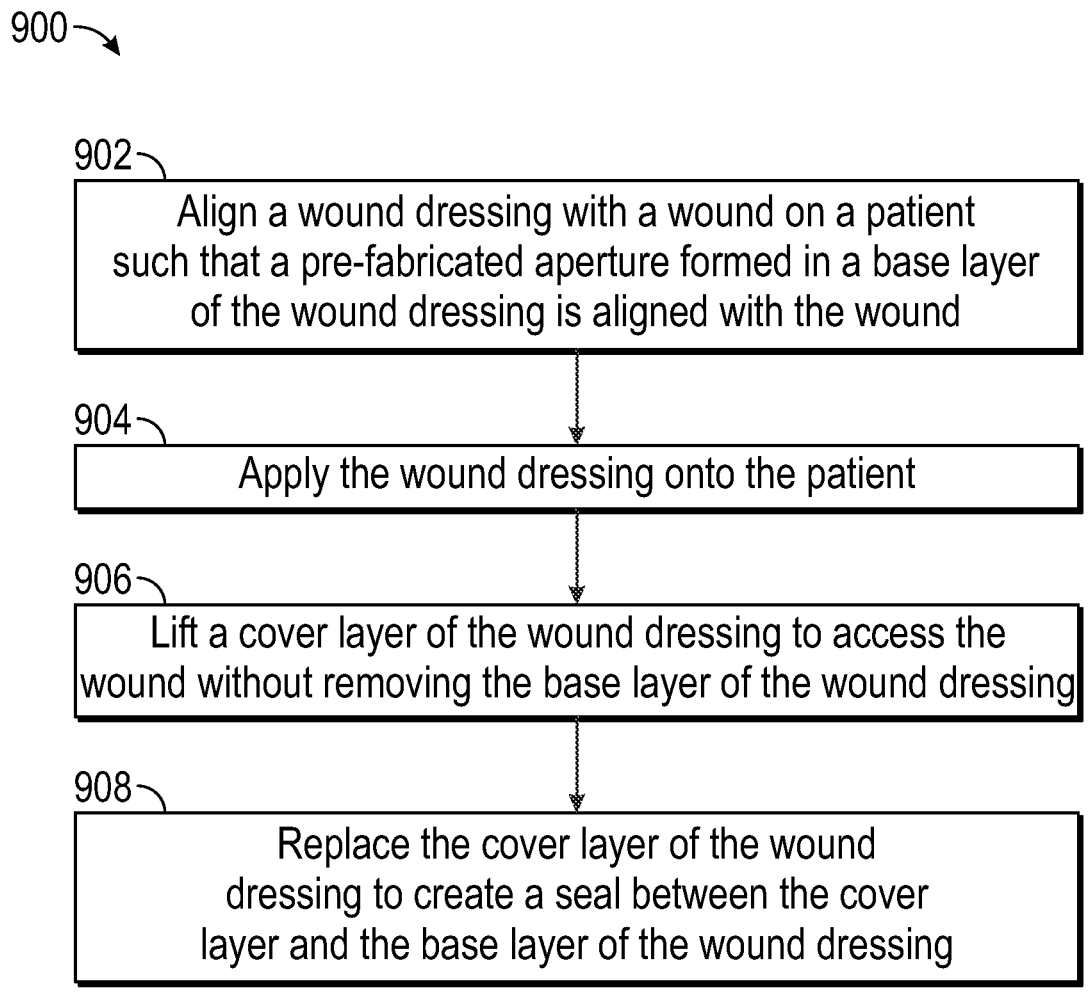
FIG. 9 is a flow chart of an example of a method to utilize a re-closable wound dressing.

Referring to FIG. 9, a flowchart is presented in accordance with an example. The method 900 is provided by way of example, as there are a variety of ways to carry out the method. The method 900 described below can be carried out using the configurations illustrated in FIGS. 1-8B, for example, and various elements of these figures are referenced in explaining example method 900. Each block shown in FIG. 9 represents one or more processes, methods or subroutines, carried out in the example method 900. Furthermore, the illustrated order of blocks is illustrative only and the order of the blocks can change according to the present disclosure. Additional blocks may be added or fewer blocks may be utilized, without departing from this disclosure. The example method 900 can begin at block 902.

At block 902, a wound dressing is aligned with a wound on a patient such that a pre-fabricated aperture formed in a base layer of the wound dressing is aligned with the wound. As described above, the wound dressing can be substantially transparent, the alignment of the wound dressing with the wound can be achieved with confidence and minimal issue.

Additionally, the pre-fabricated aperture prevents the need to cut a hole in the wound dressing which can increase safety and also ensure the borders of the base layer will not interfere with the wound.

At block 904, the wound dressing can be applied onto the patient. The base layer is adhered to the skin of the patient. The base layer includes material and adhesives such that the base layer can be attached to the patient for long periods of time, for example up to 7 days.

At block 906, a cover layer of the wound dressing is lifted to access the wound without removing the base layer of the wound dressing. In at least one example, the cover layer can be substantially transparent such that the wound is viewable through the cover layer without the need to remove the cover layer. One of a plurality of sides of the cover layer is permanently adhered to the base layer to function as a hinge. As the wound dressing utilizes the adhesive hinge, the cover layer can be lifted and replaced while minimizing the chance of the cover layer folding in on itself or being misaligned.

At block 908, the cover layer can be replaced to create a seal between the cover layer and the base layer of the wound dressing. The wound dressing prevents unwanted bacteria or other external environmental factors from affecting the healing process of the wound. The cycle of lifting and replacing the cover layer can be repeatable, for example up to 50 times, without removing the base layer. By keeping the base layer in place, the skin of the patient is not excessively irritated by removal and reapplication of adhesive. Also, the time and cost of replacing wound dressings can be drastically reduced.

As described above, in at least one example, a user can notate, on a date and dressing change management system, at least one of the following: time and/or date of accessing the wound, time and/or date of application of the wound dressing, and/or number of times the wound has been accessed. Notation of any data can ease the transition between medical staff handling the patient needs and prevent error.

Figure 10:
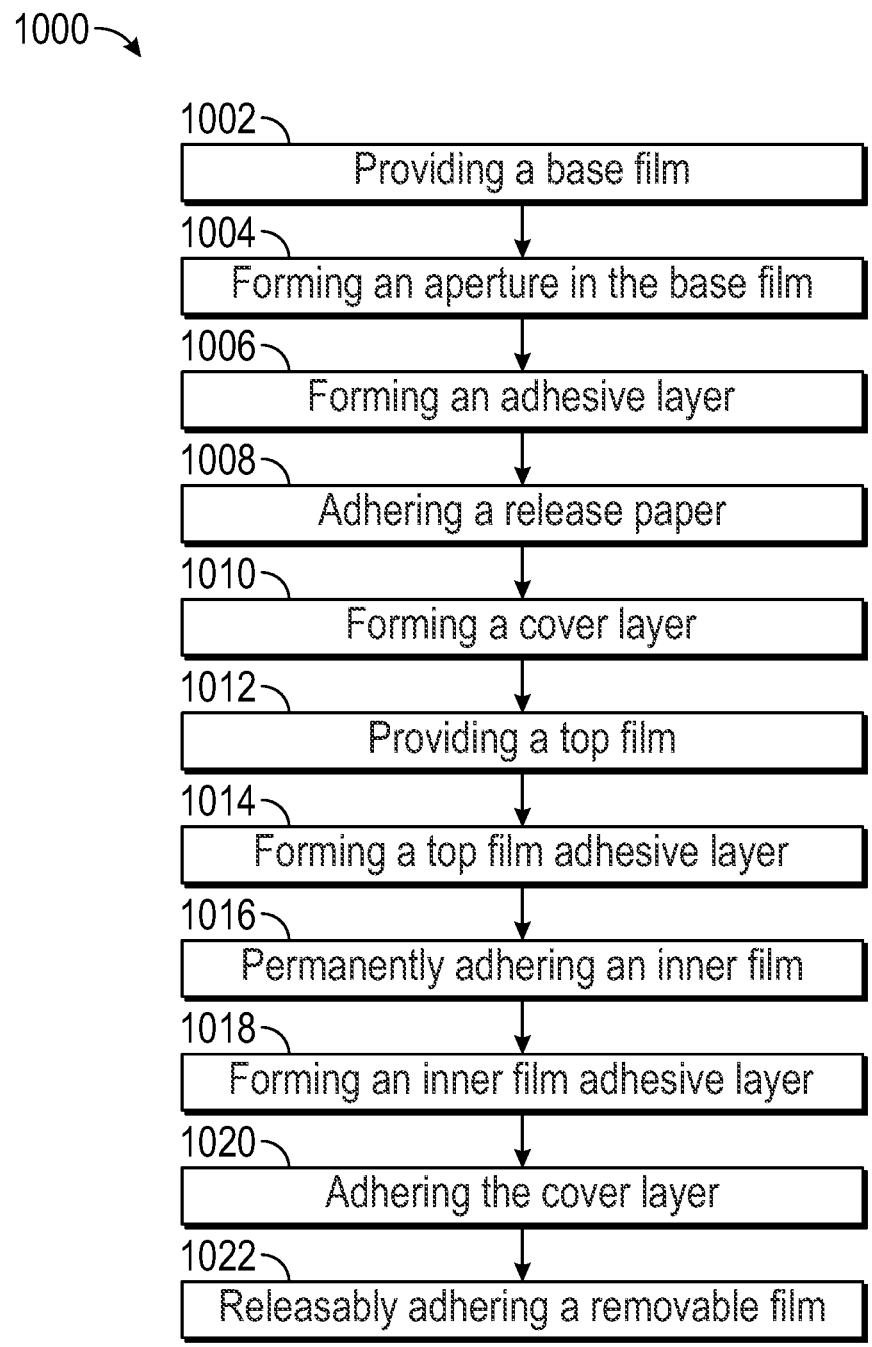
FIG. 10 is a flow chart of an example of a method of manufacturing a re-closable wound dressing.

Referring to FIG. 10, a flowchart is presented in accordance with an example. The method 1000 is provided by way of example, as there are a variety of ways to carry out the method. The method 1000 described below can be carried out using the configurations illustrated in FIGS. 1-8B, for example, and various elements of these figures are referenced in explaining example method 1000. Each block shown in FIG. 10 represents one or more processes, methods or subroutines, carried out in the example method 1000. Furthermore, the illustrated order of blocks is illustrative only and the order of the blocks can change according to the present disclosure. Additional blocks may be added or fewer blocks may be utilized, without departing from this disclosure. The example method 1000 can begin at block 1002.

At block 1002, the method can begin with providing a base film of a base layer of the wound dressing. In at least one example, the base film can be a part of a base layer as described above. While a base film is mentioned as beginning the method of manufacturing a wound dressing, in an alternative example, the method can begin with forming the cover layer. In other examples, the cover layer and base layer can be formed at substantially the same time and later joined together.

At block 1004, the method can include forming an aperture in the base film. In other instances the aperture is formed in the process of creating the base film. In yet other examples, the base layer is formed and then an aperture is formed in the base layer. When the base film has a pre-formed aperture, the other components of the base layer can be formed with a corresponding pre-formed aperture as well. In at least one example, the base layer can include two or more base films joined together by one or more adhesive layers.

At block 1006, the method can include forming an adhesive layer on a first side of the base film. The adhesive layer formed on the first side of the base film is operable to be adhered to a patient. The adhesive in the adhesive layer can be an acrylic adhesive. Additionally, the method can include providing a removable release paper to be adhered to the adhesive layer. This removable release paper can be used during shipment to preserve the adhesive layer prior to being adhered to the patient.

At block 1008, the method can include adhering a second removable release paper on a second side, opposite the first side, of the base film. The second removable release paper can be adhered using a paper that relies on bond or the second removable release paper can include an adhesive being formed thereon prior to attachment to the second side. In at least one example, the second removable release paper that is attached to the second side can be configured to be separated into two parts. In at least one example, blocks 1002 to 1008 can also be described as forming a base layer.

At block 1010, the method can include forming a cover layer being of substantially similar material as the base layer. The cover layer as described below in the other parts of the method can be formed of several layers.

At block 1012, the method can include providing a top film. The top film can be as described above. The top film can be configured to cover the aperture formed in the base film.

At block 1014, the method can include forming a top film adhesive layer on the side of the top film nearest the base layer. The top film adhesive layer is operable to allow constructing the cover layer of additional components. The top film adhesive layer can be made of a permanent adhesive. In at least one example, the top film adhesive layer can be made of an acrylic adhesive.

At block 1016, the method can include permanently adhering an inner film to the top film adhesive layer. The inner film can be made such that it is not co-extensive with the top film. In one example, the inner film can have substantially the same perimeter as the top film. In other examples, an additional tab layer can be formed between the top film and the inner film. The tab layer can be substantially smaller and extend only over a portion of the inner film that is opposite of an attachment point and/or side of the cover layer to the base layer.

At block 1018, the method can include forming an inner film adhesive layer, wherein the inner film adhesive layer comprises two regions. One of the two regions can be a first adhesive region. The first adhesive region is operable to permanently adhere the cover layer to the base layer. Another of the two regions can be a second adhesive region. The second adhesive region can be configured to releasably adhere to the base layer.

At block 1020, the method can include permanently adhering the cover layer to the base film via the first adhesive region, described above. In at least one example, the second removable release paper of the base layer can include a slot wherein at least a portion of the cover layer can be inserted through the slot, allowing the first adhesive region to permanently adhere to the base film of the base layer.

At block 1022, the method can include releasably adhering a removable film via another of the two portions.

Numerous examples are provided herein to enhance understanding of the present disclosure. A specific set of statements are provided as follows.

Statement 1: A re-closable wound dressing is disclosed comprising: a base layer operable to be attached to a skin of a patient, the base layer forming a pre-fabricated aperture through which a wound of the patient is accessible; a cover layer having a first adhesive region that, is permanently adhered to the base layer to prevent, during normal operation, the cover layer from being separated from the base layer; the cover layer having a second adhesive region that is configured to be removably coupled with the base layer; wherein the cover layer is configured to overlay the pre-fabricated aperture formed in the base layer; wherein the base layer and the cover layer are made of materials with substantially similar flexibility and stretch properties.

Statement 2: A re-closable wound dressing is disclosed according to Statement 1, wherein the base layer is polyurethane, and the cover layer is thermoplastic polyurethane.

Statement 3: A re-closable wound dressing is disclosed according to Statements 1 or 2, further comprising a date and dressing change management system, the date and dressing change management system includes a dressing portion that is configured to be adhered to the base layer and a packing portion that includes a plurality of packing change stickers.

Statement 4: A re-closable wound dressing is disclosed according to any of preceding Statements 1-3, wherein the cover layer includes a first adhesive layer comprises the first adhesive region and the second adhesive region.

Statement 5: A re-closable wound dressing is disclosed according to Statement 4, wherein when the first adhesive region is permanently adhered with the base layer it is operable to function as a hinge.

Statement 6: A re-closable wound dressing is disclosed according to Statement 5, wherein the first adhesive region comprises an acrylic adhesive and the second adhesive region comprises a silicone adhesive.

Statement 7: A re-closable wound dressing is disclosed according to Statement 4, wherein the cover layer further includes an inner film adhered to the first adhesive layer, a second adhesive layer adhered to the inner film opposite the first adhesive layer, and a top film adhered to the second adhesive layer opposite the inner film.

Statement 8: A re-closable wound dressing is disclosed according to Statement 7, wherein the cover layer further includes a removable film adhered to the first adhesive layer.

Statement 9: A re-closable wound dressing is disclosed according to Statement 7, wherein the top film is transparent.

Statement 10: A re-closable wound dressing is disclosed according to Statement 7, wherein the top film includes at least one lift tab.

Statement 11: A re-closable wound dressing is disclosed according to Statement 10, wherein the at least one lift tab comprises two lift tabs.

Statement 12: A re-closable wound dressing is disclosed according to Statement 7, wherein the cover layer further comprises a tab layer positioned between the top film and the second adhesive layer, and a tab adhesive layer positioned between the tab layer and the top film.

Statement 13: A re-closable wound dressing is disclosed according to Statement 12, wherein the top film and the tab layer include at least one lift tab that extends beyond the inner film in at least one direction.

Statement 14: A re-closable wound dressing is disclosed according to Statement 13, wherein the at least one lift tab comprises two lift tabs.

Statement 15: A re-closable wound dressing is disclosed according to Statement 7, wherein the first adhesive layer extends inwardly from edges of the top film until a recess is formed that corresponds to the pre-fabricated aperture of the base layer.

Statement 16: A re-closable wound dressing is disclosed according to Statement 4, wherein at least a portion of the first adhesive region includes acrylic adhesive, and wherein the second adhesive region is operable to form a tacky yet flexible bond between the base layer and the cover layer capable of up to 50 cycles of lifting and replacement of the cover layer to the base layer.

Statement 17: A re-closable wound dressing is disclosed according to any of preceding Statements 7-15, wherein the first adhesive layer, the inner film, and the second adhesive layer each form an aperture corresponding to the pre-fabricated aperture.

Statement 18: A re-closable wound dressing is disclosed according to any of preceding Statements 1-17, wherein the base layer includes a landing zone surrounding the pre-fabricated aperture and extending between a distance formed by an outermost edge of the base layer and an edge of the pre-fabricated aperture, wherein the landing zone is about 20% to about 65% of the distance from the pre-fabricated aperture to the outermost edge of the base layer, wherein a plurality of sides of the cover layer form a perimeter which is larger than a perimeter of the pre-fabricated aperture such that the perimeter of the cover layer is disposed in the landing zone.

Statement 19: A re-closable wound dressing is disclosed according to any of preceding Statements 1-18, wherein the base layer includes a landing zone surrounding the pre-fabricated aperture and extending between a distance formed by an outermost edge of the base layer and an edge of the pre-fabricated aperture, wherein the landing zone is about 40% to about 65% of the distance from the pre-fabricated aperture to the outermost edge of the base layer, wherein a plurality of sides of the cover layer form a perimeter which is larger than a perimeter of the pre-fabricated aperture such that the perimeter of the cover layer is disposed in the landing zone.

Statement 20: A re-closable wound dressing is disclosed according to any of preceding Statements 1-19, wherein the base layer includes a landing zone surrounding the pre-fabricated aperture and extending between a distance formed by an outermost edge of the base layer and an edge of the pre-fabricated aperture, wherein the landing zone is about 45% to about 55% of the distance from the pre-fabricated aperture to the outermost edge of the base layer, wherein a plurality of sides of the cover layer form a perimeter which is larger than a perimeter of the pre-fabricated aperture such that the perimeter of the cover layer is disposed in the landing zone.

Statement 21: A re-closable wound dressing is disclosed according to any of preceding Statements 1-20, wherein the cover layer is transparent.

Statement 22: A re-closable wound dressing is disclosed according to any of preceding Statements 1-21, wherein the base layer has a width of about 18 centimeters and a length of about 22 centimeters.

Statement 23: A re-closable wound dressing is disclosed according to any of preceding Statements 1-22, wherein the cover layer has a width of about 15 centimeters and a length of about 18 centimeters.

Statement 24: A re-closable wound dressing is disclosed according to any of preceding Statements 1-23, wherein the pre-fabricated aperture has a width of about 10 centimeters and a length of about 10 centimeters.

Statement 25: A re-closable wound dressing is disclosed according to any of preceding Statements 1-24, wherein the cover layer includes at least one lift tab which extends from one of the plurality of sides such that the cover layer is lifted from and replaced on the base layer.

Statement 26: A method is disclosed comprising: aligning a wound dressing with a wound on a patient such that a pre-fabricated aperture formed in a base layer of the wound dressing is aligned with the wound; applying the wound dressing onto the patient; lifting a cover layer of the wound dressing to access the wound without removing the base layer of the wound dressing; and replacing the cover layer of the wound dressing to create a seal between the cover layer and the base layer of the wound dressing.

Statement 27: A method is disclosed according to Statement 26, wherein a cycle of lifting and replacing the cover layer is repeatable up to 50 times without removing the base layer.

Statement 28: A method is disclosed according to Statements 26 or 27, wherein at least one of a plurality of sides of the cover layer is permanently adhered to the base layer and is operable to function as a hinge.

Statement 29: A method is disclosed according to any of preceding Statements 26-28, further comprising: notating, on a date and dressing change management system, at least one of the following: time and/or date of accessing the wound, time and/or date of application of the wound dressing, and/or number of times the wound has been accessed.

Statement 30: A method is disclosed according to any of preceding Statements 26-29, wherein the cover layer is transparent such that the wound is viewable through the cover layer.

Statement 31: A method of manufacturing a wound dressing is disclosed comprising: providing a base film; forming an aperture in the base film; forming an adhesive layer on a first side of the base film; adhering a release paper on a second side, opposite the first side, of the base film; forming a cover layer being of substantially similar material as the base layer, the forming of the cover layer comprising: providing a top film; forming atop film adhesive layer on the side of the top film nearest the base layer, permanently adhering an inner film to the top film adhesive layer, forming an inner film adhesive layer, wherein the inner film adhesive layer comprises two portions; permanently adhering at least a portion of the cover layer to the base film via one of the two portions; and releasably adhering at least a portion of the cover layer to the base film via another of the two portions.

Statement 32: A method is disclosed according to Statement 31, further comprising: providing a tab layer adhered between the top film and the top film adhesive layer by a tab film adhesive layer.

The disclosures shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims.

The invention claimed is:

1. A re-closable wound dressing comprising:
a base layer operable to be attached to a skin of a patient, the base layer forming a pre-fabricated aperture through which a wound of the patient is accessible;
a cover layer configured to overlay the pre-fabricated aperture formed in the base layer, wherein the cover layer includes a tab layer positioned between a top film and an adhesive layer, and a tab adhesive layer positioned between the tab layer and the top film.

2. The re-closable wound dressing of claim 1, wherein the base layer is polyurethane, and the cover layer is thermoplastic polyurethane.

3. The re-closable wound dressing of claim 1, further comprising a date and dressing change management system, the date and dressing change management system includes a dressing portion that is configured to be adhered to the base layer and a packing portion that includes a plurality of packing change stickers.

4. The re-closable wound dressing of claim 1, wherein the base layer and the cover layer are made of materials with substantially similar flexibility and stretch properties.

5. The re-closable wound dressing of claim 1, wherein the cover layer includes:
a first adhesive region that is permanently adhered to the base layer to prevent, during normal operation, the cover layer from being separated from the base layer;
the cover layer having a second adhesive region that is configured to be removably coupled with the base layer;
a first adhesive layer comprising the first adhesive region and the second adhesive region.

6. The re-closable wound dressing of claim 5, wherein when the first adhesive region is permanently adhered with the base layer it is operable to function as a hinge.

7. The re-closable wound dressing of claim 5, wherein the first adhesive region comprises an acrylic adhesive and the second adhesive region comprises a silicone adhesive.

8. The re-closable wound dressing of claim 1, wherein the first adhesive layer extends inwardly from edges of the top film until a recess is formed that corresponds to the pre-fabricated aperture of the base layer.

9. The re-closable wound dressing of claim 1, wherein the adhesive layer is adhered to an inner film; wherein the top film is adhered to the adhesive layer opposite the inner film.

10. The re-closable wound dressing of claim 1, wherein the cover layer further includes a removable film adhered to first adhesive layer.

11. The re-closable wound dressing of claim 1, wherein the top film is transparent.

12. The re-closable wound dressing of claim 1, wherein the top film includes at least one lift tab.

13. The re-closable wound dressing of claim 12, wherein the at least one lift tab comprises two lift tabs.

14. The re-closable wound dressing of claim 1, wherein the top film and the tab layer include at least one lift tab that extends beyond the inner film in at least one direction.

15. The re-closable wound dressing of claim 14, wherein the at least one lift tab comprises two lift tabs.

16. The re-closable wound dressing of claim 1, wherein the cover layer is transparent.

17. A method of manufacturing a wound dressing comprising:
providing a base film;
forming an aperture in the base film;
forming a cover layer, the forming of the cover layer comprising:
providing a tab layer adhered between a top film and a top film adhesive layer by a tab film adhesive layer;
permanently adhering at least a portion of the cover layer to the base film; and
releasably adhering at least a portion of the cover layer to the base film.

18. The method of claim 17, wherein forming the cover layer further comprises:
providing the top film;
forming the top film adhesive layer on the side of the top film nearest the base layer;
permanently adhering an inner film to the top film adhesive layer;
forming an inner film adhesive layer, wherein the inner film adhesive layer comprises two portions.

19. The method of claim 17, wherein the cover layer is of substantially similar material as the base film.

* * * * *